(12) United States Patent
Chandrasekaran et al.

(10) Patent No.: US 11,946,019 B2
(45) Date of Patent: Apr. 2, 2024

(54) SYNTHESIS AND USE OF 2-ETHYL-5,5-DIMETHYL-CYCLOHEXANOL AS FRAGRANCE AND FLAVOR MATERIAL

(71) Applicant: SYMRISE AG, Holzminden (DE)

(72) Inventors: Vijayanand Chandrasekaran, Holzminden (DE); Bernd Hölscher, Halle (DE)

(73) Assignee: SYMRISE AG, Holzminden (DE)

( * ) Notice: Subject to any disclaimer, the term of this patent is extended or adjusted under 35 U.S.C. 154(b) by 181 days.

(21) Appl. No.: 17/292,807

(22) PCT Filed: Nov. 12, 2019

(86) PCT No.: PCT/EP2019/080968
§ 371 (c)(1),
(2) Date: May 11, 2021

(87) PCT Pub. No.: WO2020/099372
PCT Pub. Date: May 22, 2020

(65) Prior Publication Data
US 2021/0395639 A1    Dec. 23, 2021

(30) Foreign Application Priority Data
Nov. 12, 2018  (WO) ................ PCT/EP2018/080899

(51) Int. Cl.
| | | |
|---|---|---|
| C11B 9/00 | (2006.01) | |
| C07C 29/147 | (2006.01) | |
| C07C 35/08 | (2006.01) | |
| C07C 269/00 | (2006.01) | |

(52) U.S. Cl.
CPC .......... *C11B 9/0034* (2013.01); *C07C 29/147* (2013.01); *C07C 35/08* (2013.01); *C07C 269/00* (2013.01); *C07C 2601/14* (2017.05)

(58) Field of Classification Search
CPC .................................................. C11B 9/0034
See application file for complete search history.

(56) References Cited

U.S. PATENT DOCUMENTS

| | | | |
|---|---|---|---|
| 4,187,251 A | | 2/1980 | Schleppnik |
| 4,608,445 A | * | 8/1986 | Giersch ................ C11B 9/0034 131/276 |
| 6,025,323 A | * | 2/2000 | Fehr .................... C07C 35/08 568/822 |

FOREIGN PATENT DOCUMENTS

| | | |
|---|---|---|
| DE | 1923223 A1 | 11/1969 |
| EP | 0868502 A1 | 10/1998 |
| WO | 1998013447 A1 | 4/1998 |
| WO | 2020098901 A1 | 5/2020 |

OTHER PUBLICATIONS

European Search Report dated Jun. 28, 2021 for corresponding European Application No. EP 21160197.
International Search Report and Written Opinion dated Aug. 28, 2019 for corresponding PCT Application No. PCT/EP2018/080899.
International Search Report and Written Opinion dated Feb. 21, 2020 for corresponding co-pending PCT Application No. PCT/EP2019/080968.
Normand Dufort et al., "Reduction de cetones conjuguees dans la serie acetyl methyl cyclohexene," Candian Journal of Chemistry, vol. 46, 1968, p. 1073 XP055612866.

* cited by examiner

*Primary Examiner* — Arrie L Reuther
(74) *Attorney, Agent, or Firm* — POLSINELLI PC

(57) ABSTRACT

The present invention relates to the compound 2-ethyl-5,5-dimethyl-cyclohexanol, which can impart, modify and/or enhance one or more odours selected from the group consisting of minty, fresh tobacco leaf, cresol, horse and animalistic, mixtures comprising 2-ethyl-5,5-dimethyl-cyclohexanol, and a new method for producing the same, a fragrance composition comprising 2-ethyl-5,5-dimethyl-cyclohexanol, the use of 2-ethyl-5,5-dimethyl-cyclohexanol as a fragrance, particularly for imparting, modifying and/or enhancing one or more odours selected from the group consisting of minty, fresh tobacco leaf, cresol, horse and animalistic, a perfumed product comprising 2-ethyl-5,5-dimethyl-cyclohexanol, a method for perfuming such a product and a method for modifying an olfactory impression.

19 Claims, No Drawings

SYNTHESIS AND USE OF 2-ETHYL-5,5-DIMETHYL-CYCLOHEXANOL AS FRAGRANCE AND FLAVOR MATERIAL

CROSS-REFERENCE TO RELATED APPLICATIONS

This application is a national stage application (under 35 U.S.C. § 371) of PCT/EP2019/080968, filed Nov. 12, 2019, which claims benefit of PCT Application No. PCT/EP2018/080899, filed Nov. 12, 2018, which are incorporated herein by reference in their entireties.

The present invention relates to the novel compound 2-ethyl-5,5-dimethyl-cyclohexanol, which can impart, modify and/or enhance one or more odours selected from the group consisting of minty, fresh tobacco leaf, cresol, horse and animalistic, mixtures comprising 2-ethyl-5,5-dimethyl-cyclohexanol, and a new method for producing the same, a fragrance composition comprising 2-ethyl-5,5-dimethyl-cyclohexanol, the use of 2-ethyl-5,5-dimethyl-cyclohexanol as a fragrance, a perfumed product comprising 2-ethyl-5,5-dimethyl-cyclohexanol a method for perfuming such a product and a method for modifying an olfactory impression.

Although a plurality of fragrances is already available, a general need of novel fragrances still exists in the perfume industry as the consumers frequently request novel and modern fragrances.

For the creation of novel compositions, there is a constant need of fragrances with special sensory characteristics, which are suitable to serve as a basis for the composition of novel perfumes with complex sensory character.

The search for suitable substances which led to the present invention was further impeded by the following circumstances:

- the mechanisms of the olfactory perception are not sufficiently known;
- the relationship between the special olfactory perception on the one side and the chemical structure of the corresponding fragrance on the other side are not sufficiently investigated;
- often, minor changes in the structural composition of a known fragrance cause substantial changes in the sensory characteristics and impair the tolerance of the human organism.

The primary aspect was thus to find fragrances which can be used as a fragrance e.g. for the use in the perfumery or other areas, particularly as fragrances with a minty, fresh tobacco leaf, cresol, horse and/or animalistic characteristic. Such fragrances should advantageously be suitable to perfume certain products and should further advantageously be easily produced.

Furthermore, such fragrances should preferably also fulfil one, more or advantageously all of the following aspects:
- being easily produced,
- having a strong effect in low concentration,
- having no toxic and/or allergic effect on humans, and preferably also one or both of the following aspects, where appropriate:
- largely or completely colourless,
- high stability in diverse mixtures or, respectively, preparations, wherein particularly no discoloration and/or separation and/or clouding shall occur.

The primary aspect of the present invention is achieved by a compound according to formula (I)

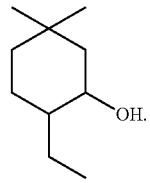

formula I

It was surprisingly found that 2-ethyl-5,5-dimethyl-cyclohexanol exhibits a minty, fresh tobacco leaf, cresol, horse and/or animalistic odour. Furthermore, it was also surprisingly found that 2-ethyl-5,5-dimethyl-cyclohexanol exhibits a sweet, raisin and minty taste.

In the state of the art, compounds with similar as well as with different chemical structure may be known for being used as a fragrance with a similar odour. However, even though there may be similar compounds, a prediction of the odour of a compound based on the chemical structure is impossible (e.g. Cell, C. S. (2006), Zur Unmöglichkeit der Geruchsvorhersage, Angewande Chemie, 118:6402-6410). Thus it is not possible to predict the odour of a compound based on the odour of a structurally highly similar compound. Likewise, it is also not possible to "design" a chemical structure based on a desired odour, which is simply synthesized and automatically exhibits the desired odour.

It was also surprisingly found that 2-ethyl-5,5-dimethyl-cyclohexanol is sufficiently stable and non-toxic.

The invention further relates to a method for producing 2-ethyl-5,5-dimethyl-cyclohexanol (formula I)

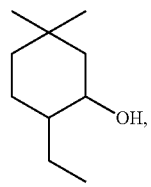

formula I comprising the following steps:
i) providing methyl-N—[(Z)-1-(2-hydroxy-4,4-dimethyl-cyclohexyl)-ethylidene amino]carbamate (formula II),

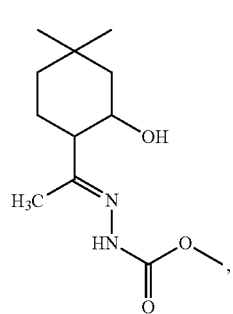

formula II ii) reacting methyl-N—[(Z)-1-(2-hydroxy-4,4-dimethyl-cyclohexyl)-ethylidene amino]carbamate (formula II) to 2-ethyl-5,5-dimethyl-cyclohexanol (formula I) with a base, preferably with potassium hydroxide. Alternatively, any other suitable base or combination of such bases may be tried and used.

Certain methods for producing 2-ethyl-5,5-dimethyl-cyclohexanol are known in the state of the art:

2-ethyl-5,5-dimethyl-cyclohexanol may be produced starting from Hagemann's ester (ethyl-2-methyl-4-oxo-2-cyclohexenecarboxylate) (Hagemann, Ber., 1893 (26), 876; Yamamoto et al., Organic Letters 2012, 14, 24, 6178-6181):

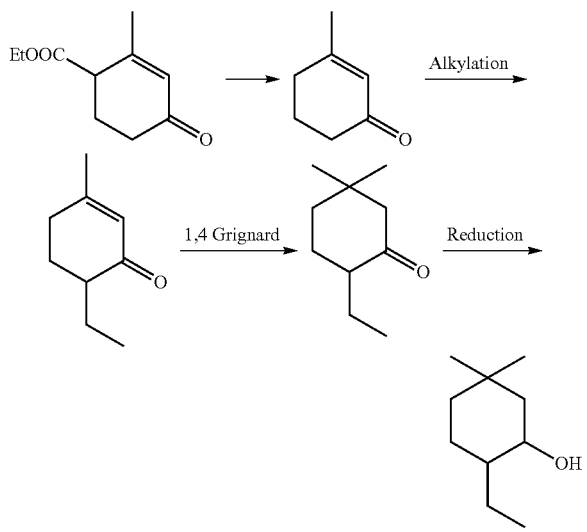

Alternatively, WO 2010/043522 A1 and WO 2009/144136 A1 describe the reduction of dimedone to 3,3-dimethylcyclo-hexan-1-one. A similar method could be applied to produce 2-ethyl-5,5-dimethyl-cyclohexanol.

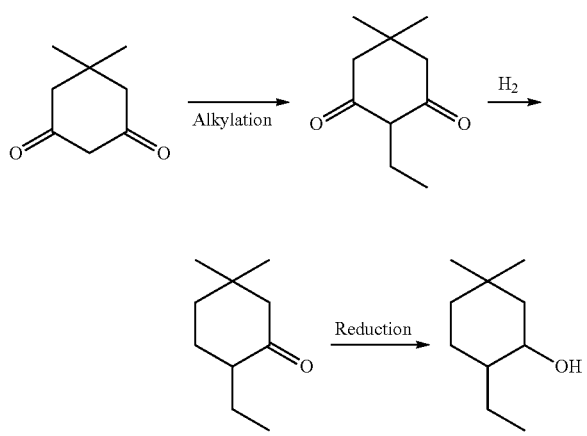

However, it has not been possible yet to produce 2-ethyl-5,5-dimethyl-cyclohexanol in such purity as with the method according to the invention. Most likely due to this fact, the sensory characteristics of 2-ethyl-5,5-dimethyl-cyclohexanol have not been discovered and described yet.

Furthermore, the method according to the invention may be more easily performed as the currently known methods and may require less reaction steps and less intermediate products which may contaminate the final product.

It is preferred that in the method according to the invention step i) is performed by providing 1-(2-hydroxy-4,4-dimethylcyclohexyl)ethan-1-one (formula III)

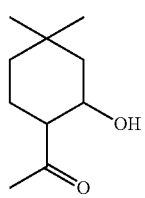

formula III and reacting 1-(2-hydroxy-4,4-dimethylcyclohexyl)ethan-1-one (formula III) (Tetrahedron Letters, 2008 (49), 6016-6018) to methyl-N—[(Z)-1-(2-hydroxy-4,4-dimethyl-cyclohexyl)-ethylidene amino] carbamate (formula II).

It is particularly preferred that the method according to the invention is a Wolff-Kishner reduction of 1-(2-hydroxy-4,4-dimethylcyclohexyl)ethan-1-one (formula III). Therefore, in the method according to the invention, the step of reacting 1-(2-hydroxy-4,4-dimethylcyclohexyl)ethan-1-one (formula III) to methyl-N—[(Z)-1-(2-hydroxy-4,4-dimethyl-cyclohexyl)-ethylidene amino] carbamate (formula II) as described above is preferably performed with a) methyl N-amino carbamate and/or hydrazine, and/or
b) one or more alcohols, preferably selected from the group consisting of lower alkyl alcohols such as methanol, ethanol, propanol, butanol, pentanol, hexanol, heptanol, octanol, nonanol and decanol, and/or
c) one or more acids, preferably selected from the group consisting of formic acid, acetic acid, propionic acid, butanoic acid, pentanoic acid, hexanoic acid, heptanoic acid, octanoic acid, nonanoic acid and decanoid acid.

Particularly preferably, the step of reacting 1-(2-hydroxy-4,4-dimethylcyclohexyl)ethan-1-one (formula III) to methyl-N—[(Z)-1-(2-hydroxy-4,4-dimethyl-cyclohexyl)-ethylidene amino]carbamate (formula II) is performed according to the following reaction scheme (IPA denotes isopropyl alcohol):

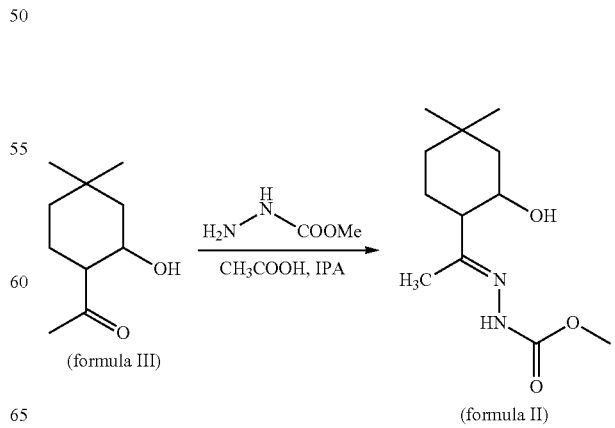

It is also preferred that step ii) of the method according to the invention is performed according to the following reaction scheme:

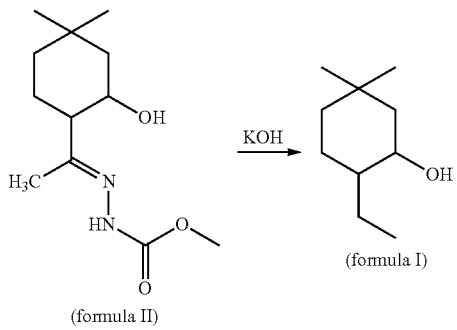 [SMILES: COC(=O)N/N=C(\C)C1CCC(C)(C)CC1O ; "KOH" ; CCC1CCC(C)(C)CC1O]
(formula II) → (formula I)

In step ii) of the method according to the invention, it is particularly preferred that the base is provided in a solvent, preferably triethylene glycol.

Even though the Wolff-Kishner reduction is known in the state of the art, it is novel to apply this reaction to produce 2-ethyl-5,5-dimethyl-cyclohexanol. Additionally, the Wolff-Kishner reduction is typically performed with hydrazine. The advantage to use methyl N-amino carbamate instead, is that the reaction time is reduced. Furthermore, hydrazine is a carcinogenic, mutagenic and reprotoxic (CMR) substance.

Preferably, the Huang Minion condition is applied to step ii). I.e. it is preferred that i) the base and the solvent, if present, is heated up to at least 80° C., preferably at least 90° C., particularly preferably at least 95° C., especially preferably at least 100° C. before or during its addition to methyl-N—[(Z)-1-(2-hydroxy-4,4-dimethyl-cyclohexyl)-ethylidene amino] carbamate (formula II)

and/or ii) step ii) is performed at at least 80° C., preferably at least 90° C., particularly preferably at least 95° C., especially preferably at least 100° C.

Applying the increased temperature for reacting methyl-N—[(Z)-1-(2-hydroxy-4,4-dimethyl-cyclohexyl)-ethylidene amino] carbamate (formula II) to 2-ethyl-5,5-dimethyl-cyclohexanol (formula I) is advantageously performed to further increase the yield of 2-ethyl-5,5-dimethyl-cyclohexanol (formula I).

Especially preferably, the method according to the invention is performed according to the following reaction scheme:

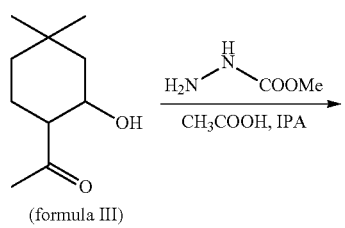
(formula III)

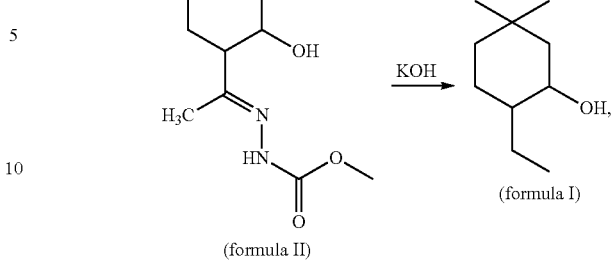
(formula II) → (formula I)

particularly preferably the Huang Minion condition (as described above) is applied.

Furthermore, it is preferred that the compound according to the invention is obtained or obtainable by a method according to the invention.

The invention further relates to a mixture comprising 2-ethyl-5,5-dimethyl-cyclo-hexanol (formula I) obtainable or obtained by a method as described herein.

As already described, it was surprisingly found that 2-ethyl-5,5-dimethyl-cyclohexanol exhibits a minty, fresh tobacco leaf, cresol, horse and/or animalistic odour. Thus, the present invention also relates to a fragrance composition comprising 2-ethyl-5,5-dimethyl-cyclohexanol (formula I), preferably wherein 2-ethyl-5,5-dimethyl-cyclohexanol (formula I) is obtained or obtainable by a method according to the invention or wherein 2-ethyl-5,5-dimethyl-cyclohexanol (formula I) is provided in the form of a mixture resulting from a method according to the invention, preferably wherein the total amount of 2-ethyl-5,5-dimethyl-cyclohexanol (formula I) in the fragrance composition is sufficient for imparting, modifying and/or enhancing an odour, preferably at least one odour selected from the group consisting of minty, fresh tobacco leaf, cresol, horse and animalistic.

Preferably, the total amount of 2-ethyl-5,5-dimethyl-cyclohexanol (formula I) in the fragrance composition according to the invention is in a range of from 0.0001 to 99.9 wt.-%, preferably in a range of from 0.001 to 99.5 wt.-%, particularly preferably 0.01 to 99 wt.-%, especially preferably 0.1 to 90 wt.-%, preferably 1 to 85 wt.-%, preferably 2 to 80 wt.-%, based on the total weight of the fragrance composition.

It is also preferred that the fragrance composition according to the invention further comprises one or more further fragrances.

Preferably, the, one or more or all of the further fragrances are selected from the group consisting of alcohols, aldehydes, ketones, ethers, esters and carboxylates, preferably alcohols and aldehydes, particularly such with a molar mass in a range of from 150 to 285 g/mol, preferably 150 to 210 g/mol.

Such further fragrances may e.g. those fragrances mentioned in S. Arctander, Perfume and Flavor Chemicals, Vol. I and II, Montclair, N.J., 1969, Selbstverlag or H. Surburg, J. Panten, Common Fragrance and Flavor Materials, 5th Ed., Wiley-VCH, Weinheim 2006. The one or more or all further fragrances may also be selected from essential oils, concretes, absolutes, resins, resinoids, balms and/or tinctures, preferably selected from the group consisting of Ambra tinktur; *Amyris* oil; *Angelica* seed oil; *Angelica* root oil; *Anise* oil; valerian oil; Basil oil; tree moss-Absolue; Bay oil; mugwort oil; *Benzoe* resin; Bergamot oil; beeswax-Absolue;

birch tar oil; bitter almond oil; savoury oil; *Bucco* leaf oil; *Cabreuva* oil; Cade oil; Calmus oil; Campher oil; *Cananga* oil; Cardamomen oil; *Cascarilla* oil; *Cassia* oil; Cassie-Absolue; *Castoreum*-absolue; cedar leaf oil; cedar wood oil; *Cistus* oil; Citronell oil; lemon oil; *Copaiva* balm; *Copaiva* balm oil; *Coriander* oil; *Costus* root oil; Cumin oil; Cypress oil; *Davana* oil; dill weed oil; dill seed oil; Eau de brouts-Absolue; oakmoss-Absolue; Elemi oil; tarragon oil; *Eucalyptus-citriodora*-oil; *Eucalyptus* oil; Fennel oil; spruce needle oil; *Galbanum* oil; Galbanumresin; *Geranium* oil; Grapefruit oil; Guajak wood oil; Gurjunbalm; Gurjunbalm oil; *Helichrysum*-Absolue; *Helichrysum* oil; ginger oil; *Iris* root-Absolue; *Iris* root oil; Jasmin-Absolue; Kalmus oil; chamomile oil blue; chamomile oil roman; carrot seed oil; Kaskarilla oil; pine needle oil; spearmint oil; caraway oil; Labdanum oil; Labdanum-Absolue; Labdanumresin; Lavandin-Absolue; Lavandin oil; Lavender-Absolue; Lavender oil; Lemongras oil; lovage oil; Lime oil distilled; Lime oil pressed; Linaloe oil; *Litsea-cubeba*-oil; lorel leaf oil; Macis oil; Majoram oil; *Mandarin* oil; Massoi bark oil; *Mimosa*-Absolue; musk corn oil; musk tincture; Muscatel-sage-oil; nutmeg oil; Myrrh-Absolue; Myrrh oil; Myrtle oil; carnation leaf oil; carnation blossom oil; Neroli oil; Olibanum-Absolue; Olibanum oil; *Opopanax* oil; Orange blossom-Absolue; Orange oil; *Origanum* oil; Palmarosa oil; Patchouli oil; *Perilla* oil; Perubalm oil; parsley leaf oil; parsley seed oil; Petitgrain oil; peppermint oil; Pepper oil; allspice oil; Pine oil; Poley oil; Rose-Absolue; rose wood oil; rose oil; Rosemary oil; sage oil dalmatinic; sage oil spanish; sandal wood oil; celery seed oil; *lavandula latifolia* oil; staranise oil; *Styrax* oil; marigold oil; fir needle oil; tee tree oil; turpentine oil; Thyme oil; Tolubalm; Tonka-Absolue; Tuberose-Absolue; Vanilla extract; violet leaf-Absolue; *Verbena* oil; Vetiver oil; juniper berry oil; wine yeast oil; wormwood oil; Wintergreen oil; Ylang oil; Ysop oil; Zibet-Absolue; cinnamon leaf oil; cinnamon bark oil.

Particularly preferably, the, one or more or all of the further fragrances may also impart, modify and/or enhance an odour selected from the group consisting of minty, fresh tobacco leaf, cresol, horse and animalistic.

Fragrance compositions according to the invention are typically liquid and homogeneous solutions at 25° C. 1013 hPa.

Fragrance compositions according to the invention can advantageously be present in concentrated form, in solutions or in modified form as described above, for the production of perfumed products according to the invention (see below).

Typically, fragrance compositions according to the invention include synthetic or preferably natural perfume oils, which are preferably gustatory and/or olfactory neutral, which contain 2-ethyl-5,5-dimethyl-cyclohexanol (formula I) in high concentrated form and optionally also solvents and/or excipients and/or additives which are commonly used in the field of perfumery.

Perfume oils are usually used for the application of a fragrance. Perfume oils are typically used for producing perfumes by adding these in (e.g. alcoholic) solutions which carry the fragrances away during vaporization and thus get them in contact with the olfactory receptors. As a result, the consumer, e.g. a human, perceives a certain odour. Such perfume oils may be used in perfumes, eau de perfume or eau de toilette. Furthermore, such perfume oils may provide a certain odour in living rooms e.g. when applied as fragrance lamp, nebulizers or diffusers. Perfume oils may further be applied in a variety of different products or, respectively, compositions ranging from shoe polish to hair shampoos, products in the sanitary field or face lotions to washing powder.

Moreover, the present invention also relates to the use of
a) 2-ethyl-5,5-dimethyl-cyclohexanol (formula I), or
b) a mixture comprising 2-ethyl-5,5-dimethyl-cyclohexanol (formula I), preferably wherein the mixture is obtained or obtainable by a method according to the invention, or
c) a fragrance composition according to the invention as a fragrance or as a fragrance composition, preferably for imparting, modifying and/or enhancing one or more odours selected from the group consisting of minty, fresh tobacco leaf, cresol, horse and animalistic.

Additionally or alternatively, 2-ethyl-5,5-dimethyl-cyclohexanol (formula I), or a mixture comprising 2-ethyl-5,5-dimethyl-cyclohexanol (formula I), wherein the mixture is obtained or obtainable by a method according to the invention, or a fragrance composition according to the invention may be used for modifying one or more olfactory impression(s) of one or more fragrance(s), preferably masking or reducing of the, one or more unpleasant olfactory impression(s) of one or more unpleasantly smelling fragrance(s), and/or enhancing of the or, respectively, one or more pleasant olfactory impression(s) of one or more pleasantly smelling fragrance(s).

The invention thus also relates to a method for modifying one or more olfactory impression(s) of one or more fragrance(s), preferably masking or reducing of the, one or more unpleasant olfactory impression(s) of one or more unpleasantly smelling fragrance(s), and/or enhancing of the or, respectively, one or more pleasant olfactory impression(s) of one or more pleasantly smelling fragrance(s), comprising the step:

mixing the one or more fragrance(s), preferably the unpleasantly and/or the pleasantly smelling fragrance(s) with
a) 2-ethyl-5,5-dimethyl-cyclohexanol (formula I), or
b) a mixture comprising 2-ethyl-5,5-dimethyl-cyclohexanol (formula I), preferably wherein the mixture is obtained or obtainable by a method according to the invention, or
c) a fragrance composition according to the invention,
wherein the amount of 2-ethyl-5,5-dimethyl-cyclohexanol (formula I) in the resulting mixture is sufficient to modify the or, respectively, one or more olfactory impression(s) of the one or more fragrance(s),
preferably wherein the amount of 2-ethyl-5,5-dimethyl-cyclohexanol (formula I) in the resulting mixture is sufficient to a) mask or reduce the or, respectively, one or more unpleasant olfactory impression(s) of one or more unpleasantly smelling fragrance(s) and/or b) enhance the or, respectively, one or more pleasant olfactory impression(s) of one or more pleasantly smelling fragrance(s).

Furthermore, the invention relates to a perfumed product comprising
a) 2-ethyl-5,5-dimethyl-cyclohexanol (formula I), or
b) a mixture comprising 2-ethyl-5,5-dimethyl-cyclohexanol (formula I), preferably wherein the mixture is obtained or obtainable by a method according to the invention, or
c) a fragrance composition according to the invention.

Products according to the invention are preferably selected from the group consisting of perfume extraits, eau de parfums, eau de toilettes, aftershaves, eau de colognes, pre-shave-products, splash-colognes and perfumed refreshing tissues, as well as for the perfuming of acid, alkaline and neutral cleaning agents such as e.g. floor cleaners, window glass cleaners, dishwashing detergents, bathroom and sanitary cleaners, scouring agents, solid and liquid toilet cleaners, carpet cleaning agents in powder and foam form, textile refreshing agents, ironing aids, liquid washing agents, washing agents in powder form, laundry pre-treatment agents such as bleaching agents, soaking agents and stain removers, fabric softeners, laundry soap, laundry tablets, disinfectants, surface disinfectants as well as of air refreshers in liquid or gel-like form or mounted on a carrier, aerosols, waxes and polishes such as furniture polish, floor waxes, shoe polish as well as body care agents such as e.g. solid and liquid soaps, shower gels, shampoos, shaving soaps, shaving foams, bath oils, cosmetic emulsions of the oil-in-water, water-in-oil and of the water-in-oil-in-water type such as e.g. body lotions, face lotions, sun protectors and sun lotions, after-sun lotions, hand lotions, foot lotions, depilatory creams and lotions, aftershave creams and lotions, tanning creams and lotions, hair-care products such as e.g. hair sprays, hair gels, solidifying hair lotions, conditioners, permanent and semipermanent hair dying agents, hair forming agents such as cold wave and hair smoothing agents, hair waters, hair lotions, deodorants, anti-transpirants such as e.g. armpit sprays, roll-ons, deodorant sticks, deodorant creams, products of decorative cosmetics such as e.g. eyeshadow, nail varnish, make-ups, lip sticks, mascara as well as of candles, lamp oils, joss sticks, insecticides, repellents and propellants.

Particularly preferably, such a product is selected from the group consisting of washing and cleaning agents, hygiene or care products, preferably in the field of body and hair care, cosmetics and home care, preferably selected from the group consisting of perfume extraits, eau de parfums, eau de toilettes, aftershaves, eau de colognes, pre-shave-products, splash-colognes, perfumed refreshing tissues, acid, alkaline or neutral cleaning agents, textile refreshing agents, ironing aids, liquid washing agents, washing agents in powder form, laundry pre-treatment agents, fabric softeners, laundry soap, laundry tablets, disinfectants, surface disinfectants, air refreshers, aerosols, waxes and polishes, body care agents, hand creams and lotions, foot creams and lotions, depilatory creams and lotions, aftershave creams and lotions, tanning creams and lotions, hair-care products deodorants, antiperspirants, products of decorative cosmetics, candles, lamp oils, joss sticks, insecticides, repellents and propellants.

Preferably, 2-ethyl-5,5-dimethyl-cyclohexanol (formula I), either present as a compound as such or in a mixture according to the invention or in a fragrance composition according to the invention, is present in the product in a sensorically effective amount.

The term "sensorically effective" as used herein is preferably meant to be understood such that the perfumed product (according to the invention) shows the sensory characteristics of 2-ethyl-5,5-dimethyl-cyclohexanol (formula I) as described herein.

It is also preferred that the total amount of 2-ethyl-5,5-dimethyl-cyclohexanol (formula I) in the product is in a range of from 0.00001 to 10 wt.-%, preferably in a range of from 0.0001 to 5 wt.-%, particularly preferably 0.001 to 2 wt.-% preferably 0.01 to 2 wt.-%, preferably 0.1 to 2 wt.-%, preferably 1 to 2 wt.-%, based on the total weight of the product.

It is also preferred that 2-ethyl-5,5-dimethyl-cyclohexanol (formula I), either present as a compound as such or in a mixture according to the invention or in a fragrance composition according to the invention, is adsorbed to a carrier which provides a fine distribution of the 2-ethyl-5, 5-dimethyl-cyclohexanol (formula I) in the product according to the invention as well as a controlled release of the same during the application. Such carriers may be porous inorganic materials such as silica gels, zeolites, gypsum, clay, clay granules, gas concrete and the like, or organic materials such as woods and cellulose based substances.

The 2-ethyl-5,5-dimethyl-cyclohexanol (formula I) or, respectively, the mixture according to the invention or, respectively, the fragrance composition according to the invention may be present in microencapsuled or spray dried form or as inclusion complexes or as extrusion product and may be added to a product (as described herein) in this form.

A microencapsulation may e.g. be performed by the so-called coacervation method using capsule materials e.g. of polyurethane containing substances or soft gelatin.

Spray dried products are preferably produced by spray drying of an emulsion or, respectively, dispersion containing the fragrance composition, wherein as carriers modified starches, proteins, dextrin and vegetable gums may be used.

Inclusion-complexes may e.g. be produced by applying dispersions of the fragrance composition and cyclodextrins or urea derivatives in a suitable solvent e.g. water.

Extrusion products can be obtained e.g. by melting the fragrance compositions with a suitable waxy substance and by extrusion with subsequent solidification, where applicable in a suitable solvent e.g. isopropanol.

Further, the invention relates to a method for perfuming a product comprising or consisting of the following steps:
i) providing
  a) 2-ethyl-5,5-dimethyl-cyclohexanol (formula I), or
  b) a mixture comprising 2-ethyl-5,5-dimethyl-cyclohexanol (formula I), preferably wherein the mixture is obtained or obtainable by a method according to the invention, or
  c) a fragrance composition according to the invention
ii) adding the compound or mixture or fragrance composition provided in step i) to the product to be perfumed, in a sensorically effective amount, preferably an amount sufficient for imparting, modifying and/or enhancing an odour, preferably at least one odour selected from the group consisting of minty, fresh tobacco leaf, cresol, horse and animalistic.

As also results from the above, 2-ethyl-5,5-dimethyl-cyclohexanol (formula I), the mixture according to the invention or the fragrance composition according to the invention are particularly suitable to modify odours, preferably (a) for masking or reducing the or one or more unpleasant olfactory impression(s) of one or more unpleasant smelling substances, and/or (b) for enhancing the or one or more pleasant olfactory impression(s) or one of one or more pleasant smelling substances.

Further features and advantages of the invention result from the subsequent description of preferred application examples.

EXAMPLES

Example 1: Synthesis of Methyl N—[(Z)-1-(2-hydroxy-4,4-dimethyl-cyclohexyl) Ethylidene Amino] Carbamate (Formula II)

To a solution of 1-(2-hydroxy-4,4-dimethylcyclohexyl) ethan-1-one (5.0 g) in Isopropanol (75 mL), portion wise methyl N-amino carbamate (2.95 g) was added followed by catalytic amount of acetic acid. Reaction mixture was refluxed for 4-5 h. At room temperature, reaction mixture was quenched with cold water, compound extracted in MTBE (50 mL×3), combined organic later washed with water until neutral pH, dried with MgSO$_4$ and evaporated to get crude followed by Kugelrohr distillation (150° C., 0.9 mbar) gave the title compound 4.3 g, 61%.

$^1$H NMR (600 MHz, CDCl$_3$) δ 7.71 (s, 1H), 3.98 (td, J=10.8, 3.9 Hz, 1H), 3.82 (s, 3H), 2.10 (ddd, J=13.3, 9.6, 3.6 Hz, 1H), 1.83 (s, 3H), 1.76 (dddd, J=10.5, 8.5, 5.3, 2.6 Hz, 2H), 1.45-1.40 (m, 1H), 1.38 (qd, J=12.9, 3.1 Hz, 1H), 1.24 (td, J=13.4, 12.1, 3.9 Hz, 1H), 1.20 (t, J=13.2, 12.4 Hz, 1H), 0.97 (s, 3H), 0.94 (s, 3H).

$^{13}$C NMR (151 MHz, CDCl$_3$) δ 155.15, 154.62, 67.69, 54.63, 52.96, 46.55, 38.46, 32.87, 32.01, 25.25, 25.15, 13.48.

GC-MS: 242, 209, 168, 143, 111, 83, 69, 55, 41, 29

Example 2: Synthesis of 2-ethyl-5,5 dimethyl-cyclohexanol (Formula I)

To a solution of KOH (3.89 g) in triethylene glycol (30 mL), at 100° C. methyl-N—[(Z)-1-(2-hydroxy-4,4-dimethyl-cyclohexyl)-ethylidene amino] carbamate (4.3 g) was added and maintained until consumption of starting material. At room temperature, reaction mixture was further diluted with water (30 mL), compound extracted in MTBE (30 mL×3), combined organic later washed with water, dried with MgSO$_4$ and evaporated to get crude. Crude product was purified by column chromatography (cyclohexane:ethyl acetate 10:1) gave the required product (weight=1.1 g, 39%).

$^1$H NMR (400 MHz, CDCl$_3$) δ 3.40 (ddd, J=11.2, 9.4, 4.4 Hz, 1H), 1.87-1.76 (m, 1H), 1.71-1.64 (m, 2H), 1.35 (dq, J=11.7, 2.5 Hz, 1H), 1.21-1.07 (m, 4H), 1.06-0.98 (m, 1H), 0.94 (s, 3H), 0.92 (t, J=7.6 Hz, 3H), 0.89 (s, 3H).

$^{13}$C NMR (101 MHz, CDCl$_3$) δ 71.52, 48.72, 46.87, 38.63, 32.98, 32.25, 25.85, 25.08, 24.54, 10.93.

GC-MS: 141, 123, 85, 69, 41

Application Example 1: Fragrance Composition without 2-Ethyl-5,5-Dimethyl-Cyclohexanol (Formula I)

| Ingredient | Amount [wt.-%] |
|---|---|
| Agrumex LC | 1.00 |
| Amarocit ® 10% in DPG | 1.00 |
| Calone 1951 10% in DPG | 1.00 |
| Cedar wood oil | 1.00 |
| Cedrol Krist | 5.00 |
| Citral 10% in DPG | 1.00 |
| Citonellol | 0.50 |
| Cumarin | 1.00 |
| Cyclogalbanate ® 10% ig in DPG | 1.50 |
| Dihydromyrcenol | 8.00 |
| Farenal ® 10% in DPG | 0.50 |
| Galbex 10% in DPG | 2.50 |
| Geraniol | 8.00 |
| Geranyl nitrile | 4.00 |
| Hedion | 9.00 |
| Helional | 2.00 |
| Heliotropin | 0.50 |
| Hexenol cis-3 10% in DPG | 1.50 |
| Hexenylsalicylate cis-3 | 1.00 |
| Beta-Ionon | 0.50 |
| Iso E Super | 6.50 |
| Isodamascon ® 10% in DPG | 1.00 |
| Isogalbanate | 2.00 |

-continued

| Ingredient | Amount [wt.-%] |
|---|---|
| Isoraldein 70 | 2.00 |
| Lavandinoel Grosso Nat. | 1.50 |
| Lilial | 2.00 |
| Linalool | 2.00 |
| Linalylacetate | 4.00 |
| Mandarin oil Brazil. green | 5.00 |
| Vanillin | 0.50 |
| Veloutone 10% in DPG | 2.00 |
| DPG | 21.00 |
| Total | 100.00 |

The olfactory impression of the fragrance composition (i.e. without 2-ethyl-5,5-dimethyl-cyclohexanol (formula I)) is described as flowery, woody, slightly fresh.

According to the perfumers, the olfactory impression of the fragrance composition becomes more fresh, more minty and with a slight tobacco smell when 5 wt.-% of 2-ethyl-5,5-dimethyl-cyclohexanol (formula I) is added.

The invention claimed is:

1. A compound according to formula (I) (2-ethyl-5,5-dimethyl-cyclohexanol)

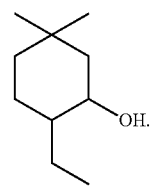

formula I

2. The compound according to claim 1, wherein the compound is obtainable by a method comprising:
   i) providing methyl-N—[(Z)-1-(2-hydroxy-4,4-dimethyl-cyclohexyl)-ethylidene amino] carbamate (formula II),

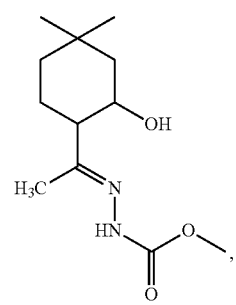

formula II ii) converting the methyl-N—[(Z)-1-(2-hydroxy-4,4-dimethyl-cyclohexyl)-ethylidene amino] carbamate (formula II) to 2-ethyl-5,5-dimethyl-cyclohexanol (formula I) with a base.

3. The compound according to claim 2, wherein step i) of the method is performed by providing 1-(2-hydroxy-4,4-dimethylcyclohexyl)ethan-1-one (formula III)

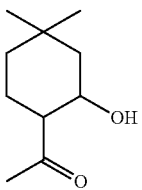

formula III and converting the 1-(2-hydroxy-4,4-dimethylcyclohexyl)ethan-1-one (formula III) to the methyl-N—[(Z)-1-(2-hydroxy-4,4-dimethyl-cyclohexyl)-ethylidene amino] carbamate (formula II).

4. The compound according to claim 2, wherein the base in step ii) is provided in a solvent.

5. The compound according to claim 2, wherein the base is heated to at least 80° C. before or during addition to the methyl-N—[(Z)-1-(2-hydroxy-4,4-dimethyl-cyclohexyl)-ethylidene amino] carbamate (formula II) and/or wherein step ii) of the method is performed at a temperature of least 80° C.

6. A mixture comprising the compound according to claim 2.

7. A method for perfuming a product comprising adding the 2-ethyl-5,5-dimethyl-cyclohexanol (formula I) according to claim 2 to the product in a sensorially effective amount.

8. The method according to claim 7, wherein the 2-ethyl-5,5-dimethyl-cyclohexanol (formula I) is added to the product in an amount sufficient to impart, modify, and/or enhance an odour selected from minty, fresh tobacco leaf, cresol, horse and animalistic.

9. A method for modifying one or more olfactory impression(s) of one or more fragrance(s) comprising combining a sensorially effective amount of the 2-ethyl-5,5-dimethyl-cyclohexanol (formula I) according to claim 2 with the one or more fragrance(s).

10. A perfumed product comprising the 2-ethyl-5,5-dimethyl-cyclohexanol (formula I) according to claim 1.

11. The perfumed product according to claim 10, wherein the product is selected from washing and cleaning agents, hygiene or care products, perfumed refreshing tissues, acid, alkaline or neutral cleaning agents, textile refreshing agents, ironing aids, liquid washing agents, washing agents in powder form, laundry pre-treatment agents, fabric softeners, laundry soap, laundry tablets, disinfectants, surface disinfectants, air refreshers, aerosols, waxes and polishes, body care agents, hand creams and lotions, foot creams and lotions, depilatory creams and lotions, aftershave creams and lotions, tanning creams and lotions, hair-care products, deodorants, anti-perspirants, products of decorative cosmetics, candles, lamp oils, joss sticks, insecticides, repellents, and propellants.

12. The perfumed product according to claim 10, wherein the 2-ethyl-5,5-dimethyl-cyclohexanol (formula I) in the product is in an amount of 0.00001 to 10 wt.-%, based on the total weight of the product.

13. A method for producing 2-ethyl-5,5-dimethyl-cyclohexanol (formula I)

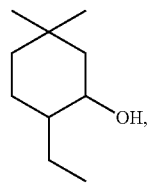

formula I comprising:
i) providing methyl-N—[(Z)-1-(2-hydroxy-4,4-dimethyl-cyclohexyl)-ethylidene amino] carbamate (formula II),

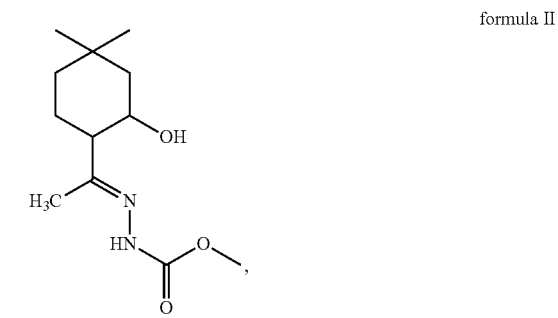 [SMILES: COC(=O)N/N=C(\C)C1CCC(C)(C)CC1O]

formula II ii) converting the methyl-N—[(Z)-1-(2-hydroxy-4,4-dimethyl-cyclohexyl)-ethylidene amino] carbamate (formula II) to 2-ethyl-5,5-dimethyl-cyclohexanol (formula I) with a base.

14. The method according to claim 13, wherein step i) is performed by providing 1-(2-hydroxy-4,4-dimethylcyclohexyl)ethan-1-one (formula III)

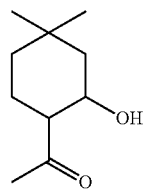

formula III and converting the 1-(2-hydroxy-4,4-dimethylcyclohexyl)ethan-1-one (formula III) to methyl-N—[(Z)-1-(2-hydroxy-4,4-dimethyl-cyclohexyl)-ethylidene amino] carbamate (formula II).

15. The method according to claim 13, wherein the base in step ii) is provided in a solvent.

16. The method according to claim 13, wherein the base is heated to at least 80° C. before or during addition to the methyl-N—[(Z)-1-(2-hydroxy-4,4-dimethyl-cyclohexyl)-ethylidene amino] carbamate (formula II) and/or wherein step ii) is performed at a temperature of at least 80° C.

17. A fragrance composition comprising the 2-ethyl-5,5-dimethyl-cyclohexanol (formula I) according to claim 1 in an amount sufficient to enhance an odour selected from minty, fresh tobacco leaf, cresol, horse, and animalistic.

18. The fragrance composition according to claim 17, wherein the total amount of the 2-ethyl-5,5-dimethyl-cyclohexanol (formula I) in the fragrance composition is 0.0001 to 99.9 wt.-%, based on the total weight of the fragrance composition.

19. A method for imparting, modifying, and/or enhancing one or more odours selected from minty, fresh tobacco leaf, cresol, horse, and animalistic comprising incorporating the 2-ethyl-5,5-dimethyl-cyclohexanol (formula I) according to claim 1 into a composition in an amount sufficient to impart, modify, and/or enhance the one or more odours selected from minty, fresh tobacco leaf, cresol, horse, and animalistic.

* * * * *